US011996192B2

(12) United States Patent
Friou et al.

(10) Patent No.: US 11,996,192 B2
(45) Date of Patent: May 28, 2024

(54) DIGITAL HUMAN REPLICAS FOR REMOTE PATIENT MONITORING AND WELLNESS SERVICES

(71) Applicant: SANCTIPHI TECH INC, Miami, FL (US)

(72) Inventors: Diana Stiles Friou, Orlando, FL (US); Edward Lee Koch, San Rafael, CA (US)

(73) Assignee: SANCTIPHI TECH INC, Miami, FL (US)

( * ) Notice: Subject to any disclaimer, the term of this patent is extended or adjusted under 35 U.S.C. 154(b) by 230 days.

(21) Appl. No.: 17/398,948

(22) Filed: Aug. 10, 2021

(65) Prior Publication Data
US 2022/0068475 A1    Mar. 3, 2022

Related U.S. Application Data

(60) Provisional application No. 63/103,519, filed on Aug. 11, 2020.

(51) Int. Cl.
| | |
|---|---|
| G16H 40/67 | (2018.01) |
| G16H 10/60 | (2018.01) |
| G16H 15/00 | (2018.01) |
| G16H 20/10 | (2018.01) |
| G16H 40/20 | (2018.01) |
| A61B 8/00 | (2006.01) |
| G16H 10/20 | (2018.01) |
| G16H 20/30 | (2018.01) |
| G16H 50/70 | (2018.01) |

(52) U.S. Cl.
CPC .............. *G16H 40/67* (2018.01); *G16H 10/60* (2018.01); *G16H 15/00* (2018.01); *G16H 20/10* (2018.01); *G16H 40/20* (2018.01); *A61B 8/565* (2013.01); *G16H 10/20* (2018.01); *G16H 20/30* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 10,178,953 B2 | 1/2019 | Ji et al. | |
| 2013/0346109 A1 * | 12/2013 | Gunn | G16Z 99/00 705/3 |

(Continued)

OTHER PUBLICATIONS

Hung et al. ("Wearable medical devices for tele-home healthcare," The 26th Annual International Conference of the IEEE Engineering in Medicine and Biology Society, San Francisco, CA, USA, 2004, pp. 5384-5387) (Year: 2004).*

*Primary Examiner* — Christopher B Tokarczyk
(74) *Attorney, Agent, or Firm* — Kerr IP Group, LLC

(57) ABSTRACT

A remote patient monitoring system and method collects patient healthcare information to create a digital healthcare representation. The remote patient monitoring system communicatively couples various medical devices through a remote healthcare gateway (RHG) to a cloud-base management server, so that the output of those medical devices may be integrated into the digital healthcare representation in real-time. A subset of the digital healthcare representation is used to generate a replicate model which is communicatively coupled to a third party cloud component.

18 Claims, 12 Drawing Sheets

(56) References Cited

U.S. PATENT DOCUMENTS

2014/0006047 A1* 1/2014 Amathnadu ........... G16H 10/60
  705/2
2015/0216448 A1  8/2015 Lotan et al.
2019/0336085 A1* 11/2019 Kayser ................... A61B 5/447

* cited by examiner

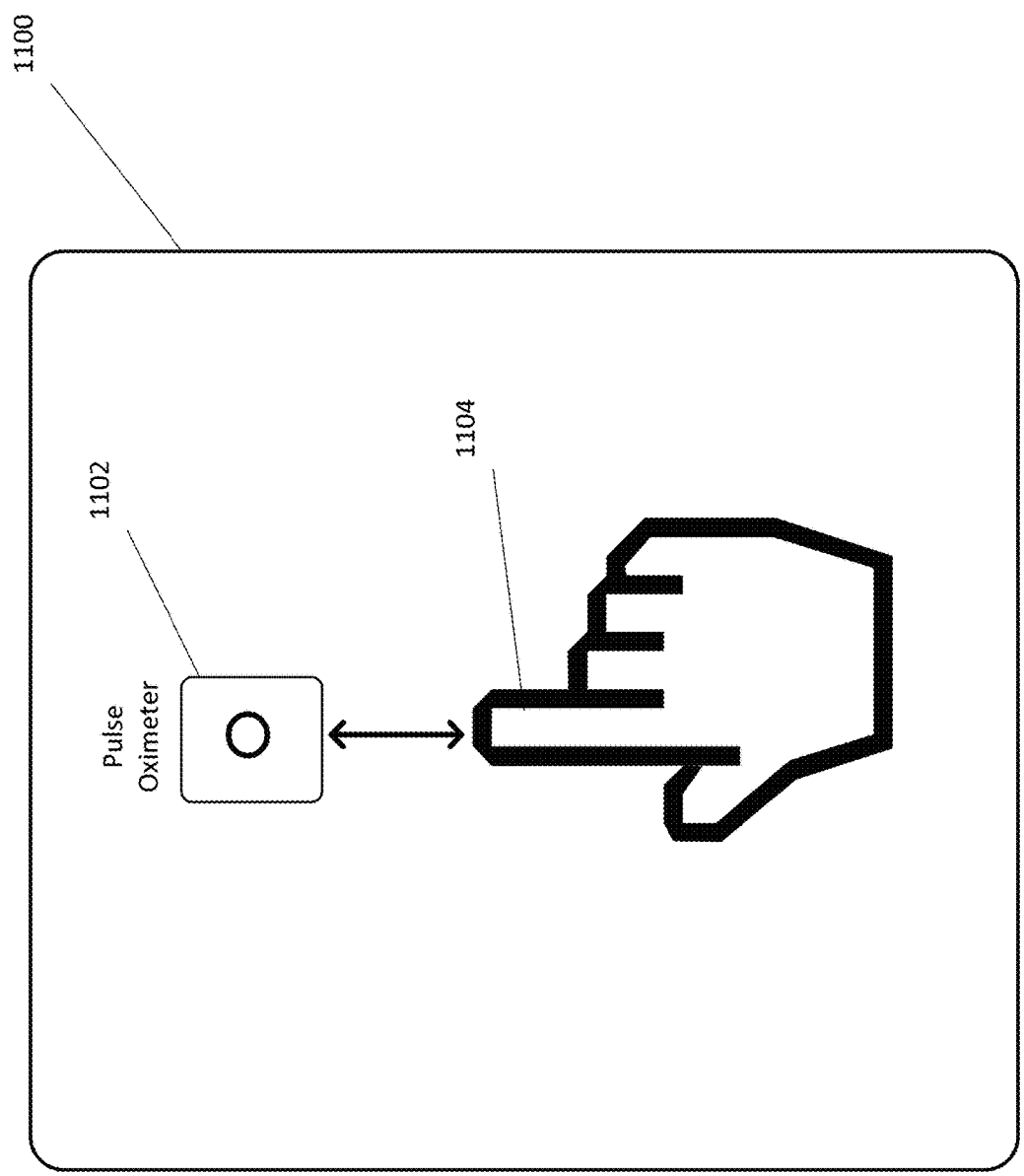

DIGITAL HUMAN REPLICAS FOR REMOTE PATIENT MONITORING AND WELLNESS SERVICES

CROSS-REFERENCE

This patent application claims the benefit of provisional patent application 63/103,519 filed on Aug. 11, 2020, entitled SYSTEM AND METHOD FOR PROVIDING TELEHEALTH AND REMOTE PATIENT MONITORING and is hereby incorporated by reference in this patent application.

FIELD

The present disclosure relates to a system and method for generating a replica of a patient based on a composite of digital models. More specifically, the system and method generates the digital patient replica from networked medical devices collecting patient biometrics, electronic health records (EHR), healthcare payer systems, and systems that store genome/exome information, all of which are communicated over a network to a cloud server.

BACKGROUND

Many chronic disease patients are required to make repeated clinical visits, e.g., every four to twelve weeks depending on the severity or aggressiveness of the disease. Regretfully, these periodic outpatient appointments provide limited treatment options and results because these services do not allow doctors or medical providers to monitor and control the patients progress or decline. Also, outpatient care cannot account for surges in patient needs when environmental factors or other such factors negatively impact a patient's condition.

Home care services and emergency medical services provide relief from surging or emergent patient needs, but they are costly. An alternative to home care services is telehealth, which has also failed to adequately serve patients because of the low quality of doctor-patient interaction or because of an inability to provide the appropriate level of health care services.

Thus, there is a need for a system and method that continuously monitors patients remotely and so the system and method is not restricted to hospital and other medical facilities.

SUMMARY

A remote patient monitoring system and method are described herein. In the illustrative embodiment, the remote patient monitoring system includes a remote healthcare gateway (RHG) mobile application executed on a mobile device, a remote healthcare cloud component, a medical device, a database associated with the remote healthcare cloud component, a digital healthcare representation associated with a patient, and a replicate model. The RHG mobile application is communicatively coupled to the remote healthcare cloud component over a wide area network (WAN). The mobile device is associated with the patient. The medical device may be one of a thermometer, a sphygmomanometer, an electrocardiogram machine, a pulse oximeter, a weight scale, an ultra sound machine, a glucose monitor, a skin analysis machine, a stethoscope, an autoscope, an orthopedic corrective therapy device, and a wellness monitoring wearable. The database associated with the remote healthcare cloud component receives biometric data input from the medical device, and stores patient healthcare data items. The patient healthcare data items may include provider health records, electronic health records, genomic data, exomic data, medical device readings, medical device reports, a list of patient allergies, an inventory of patient medications, pharmacy number, prescriber, strength, dosage, purpose, side effects, drug-drug interactions, indications to alert clinicians to reactions, quantity remaining, timing for refills, questionnaire responses, and transaction logs.

The digital healthcare representation includes a plurality of patient healthcare data items including biometric data input from the medical device. The digital healthcare representation is stored on either the RHG mobile application, the remote healthcare cloud component, or any combination thereof. The replicate model of the digital healthcare representation includes a subset of data items from the digital healthcare representation and is presented to a third-party cloud component. The remote healthcare cloud component generates patient tasks based upon the digital healthcare representation and communicates the plurality of patient tasks to the RHG mobile application.

In another illustrative embodiment, the subset of data items from the digital healthcare representation is based on a patient input.

In yet another embodiment, the remote healthcare cloud component includes a system log for the RHG mobile application activity associated with the patient.

In a further embodiment, the remote healthcare cloud component receives historic data associated with the patient from one or more healthcare providers via a fast healthcare interoperability resources.

In a still further embodiment, the RHG generates a plurality of alerts including at least one of a task alert, a security alert, a message alert, and a device alert.

In an even further embodiment, the plurality of patient tasks includes at least one of an instruction to perform an exercise, an instruction to take a medication, and an instruction to attend an appointment.

FIGURES

The present disclosure will be more fully understood by reference to the following drawings which are presented for illustrative, not limiting, purposes.

FIG. 11 shows an illustrative Augmented Reality (AR) medical device tutorial in the RHG application.

DESCRIPTION

Figure 1:
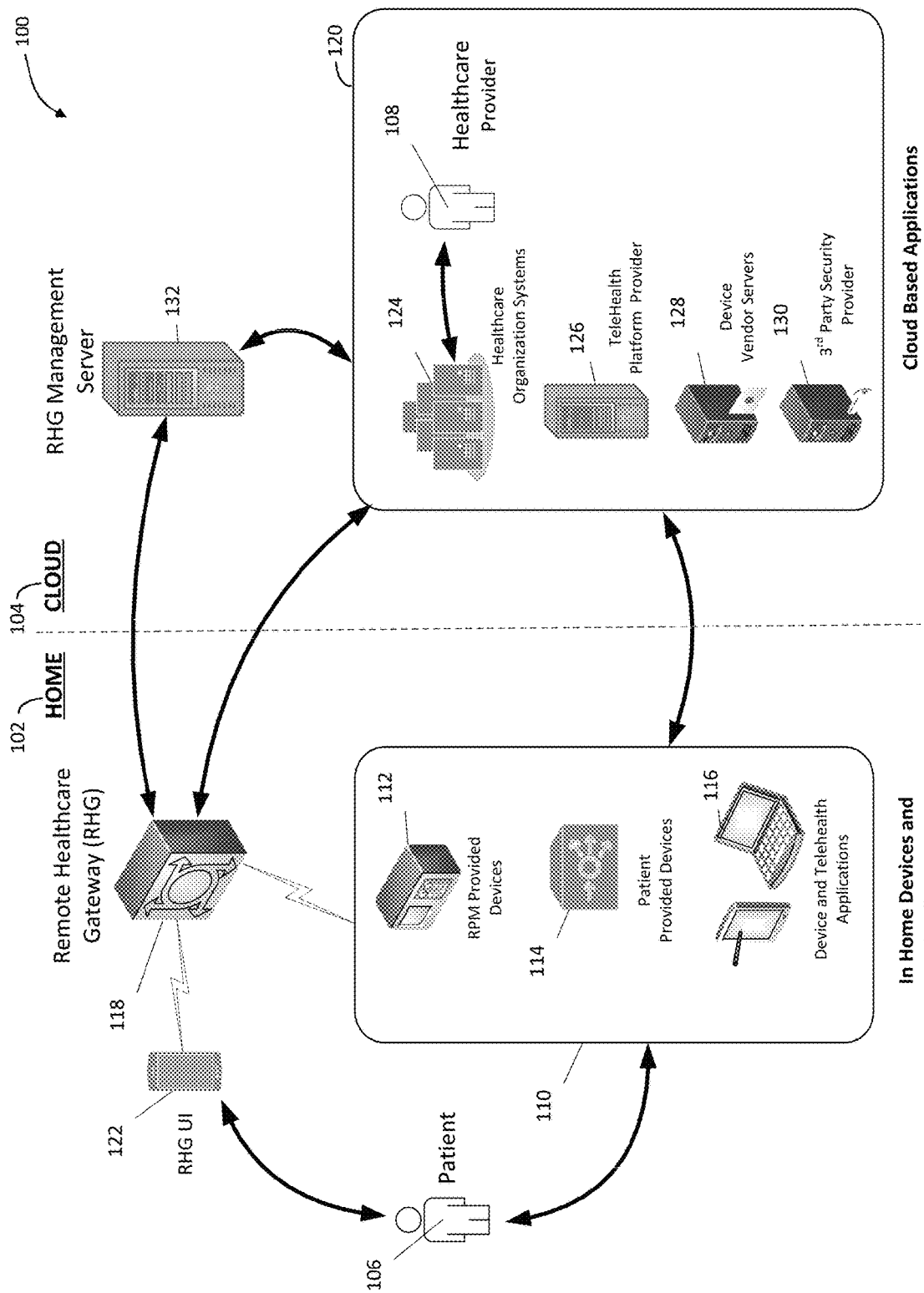
FIG. 1 shows an illustrative a diagram of an illustrative remote patient monitoring (RPM) system.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and methods described herein may vary as to configuration and as to details. The following detailed description of the illustrative embodiments includes reference to the accompanying drawings, which form a part of this application. The drawings show, by way of illustration, specific embodiments in which the embodiments may be practiced. It is to be understood that other embodiments may be utilized and structural changes may be made without departing from the scope of the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

A method and system for providing improved remote patient monitoring is described herein. These methods and systems operate by modeling and maintaining the current health and wellness information of a patient as a digital healthcare representation, which is also referred to as a "Sealthies." Note, for purposes of this patent the terms "digital healthcare representation" and "Sealthie" are used interchangeably.

The term "Sealthie" borrows from the Urban Dictionary term "Sealth" (meaning safe and healthy) and the term "Selfie" (a picture one takes of oneself). Within the context of this patent, a Sealthie is defined as a digital healthcare representation that includes a representation of a patient having a variety of healthcare information and biometric monitoring data related to that patient's health and wellness. This information is measured and updated in real-time by medical devices or other instruments connected or accessible to the patient.

The digital healthcare representation or Sealthie may also be modeled from historical, healthcare, genomic, exomic, and other types of health-related information obtained from other sources. Exemplary health-related information may include body temperature, blood pressure, EKG readings, blood oxygen saturation, sleep times, sleep quality, exercise, genome data, exome data, historical data from EHR, and healthcare payer systems. More generally, the Sealthie may contain, include, or be modeled from any information that is relevant to the health of the patient or useful to the patient, wellness coaches, and healthcare providers. The Sealthie is updated remotely and automatically and made available to other cloud-based healthcare applications upon request and/or patient consent. Thus, the Sealthie provides patients the ability to control who has access to their information.

As a cloud-based solution, a patient's Sealthie is a software module that may be instantiated in various network locations including servers, a cloud, and devices in the patient's home. The Sealthie disclosed herein is a software entity that supports remote patient monitoring and telehealth services, while providing patient control over the Sealthie by selecting which data elements of the Sealthie can be made available to healthcare organizations. Such selections result in a "replicate model" of the Sealthie that is a vehicle for distributing patient data.

The figures presented and described herein demonstrate how the Sealthie is maintained for and through remote patient monitoring, telehealth infrastructures used within the healthcare industry, and patient engagement, which all operate together to increase patients' control over their healthcare experience. The Sealthie provides a single, consolidated representation of the past and present state of a patient's health. This consolidated representation can be maintained and controlled by the patient, without relying on third-party systems. This autonomy provides patients unrestricted access to, as well as control over, their healthcare and wellness information. The Sealthie interfaces with remote patient monitoring services, telehealth services, and third-party wellness and healthcare applications. Thus, any application that needs access to a patient's health information may receive the information, with the patient's consent, using the Sealthie and its interface to the patient. In the complex healthcare ecosystem, Sealthie interfaces reduce barriers to accessing healthcare, make healthcare access more transparent, and engage and empower patients to control their wellness and healthcare journey.

As used herein, the term "telehealth" is defined as the distribution of health-related services and information via electronic and telecommunication technologies. Telehealth enables long-distance patient-clinician services, such as interaction, examination, care, advice, reminders, education, intervention, monitoring, and remote admissions. These patient-clinician services include the use of medical devices (usually biometric in nature), such as stethoscopes, blood pressure cuffs, pulse oximeters, etc. More generally, telehealth allows healthcare providers to service and treat patients without the need for them to be in physical proximity, which results in more timely, convenient, and cost effective patient treatments.

Remote patient monitoring is a frequent requirement for the provision of telehealth services. As used herein, the term "remote patient monitoring" is defined as any technology that enables monitoring of patients outside of conventional clinical settings, such as in the home or other remote location, which may increase patient access to care and decrease healthcare delivery costs. Medical devices used for remote patient monitoring are frequently biometric in nature, because these medical devices measure physiological activity.

As used herein, the term "biometric monitoring" is separate and distinct from biometric authentication, and defined as the tracking of patient characteristics related to human traits and physiological parameters, such as temperature, skin conductance, brain activity, heart rate dynamics, temperament, motivation, etc. The wellness industry develops and uses devices measuring these patient characteristics, and terms them "wearables." Wearables are also used to assess other patient characteristics, such as emotions and behavior. Wearables and other medical devices that receive FDA approval are classified as "medical grade."

Referring now to FIG. 1, there is shown a diagram of an illustrative remote patient monitoring (RPM) system 100.

The illustrative RPM system 100 is divided into two (2) domains: a home domain 102 and a cloud domain 104. The RPM system 100 enables a patient 106 in the home domain 102 to receive healthcare services from a healthcare provider 108 through the cloud domain 104. This RPM system operates under the basic assumption that while the healthcare provider 108 can be a person not physically located in the cloud domain 104, such healthcare person is not located in the patient's home domain 102 and that the home domain 102 is not necessarily a clinical locale or setting.

The home dome 102 represents the remote locale where the patient 106 is located, but is not restricted to a patient's actual home, and may include any locale where the patient 106 is located (e.g., office or school). Several system elements may exist in this home domain 102 that are commercial off the shelf (COTS) devices and/or software (SW) applications, which together are termed home domain components 110. The COTS devices or SW applications 110 may be provided by one or more vendor for the purpose of measuring a patient's health state (i.e., physiological functions) and facilitating the provision of healthcare and wellness services.

In the illustrative embodiment, the COTS devices or SW applications 110 include remote patient monitoring devices 112, patient provided devices 114, and telehealth applications 116. The remote patient monitoring devices 112 include any devices provided by healthcare providers, a healthcare delivery organization, or other third-party service providers that are installed and interfaced to the patient 106 for the purposes of measuring healthcare and/or biometric related data (i.e., physiological functions) from the patient 106.

In some embodiments, the remote patient monitoring devices 112 may include a thermometer, a sphygmomanometer, an electrocardiogram machine, a pulse oximeter, a weight scale, an ultrasound machine, a glucose monitor, a skin analysis machine, a stethoscope, an autoscope, an orthopedic corrective therapy device, and a wellness monitoring wearable. The patient provided devices 114 include any devices that are purchased by the patient 106 for the patient's own purposes, such as biometric monitoring devices, FDA class I medical devices, FDA class II medical devices, activity monitors, wireless weight scales, and healthcare/wellness SW applications. The telehealth application 116 may be specific to a remote patient monitoring device 112 or patient provided device 114, thus the telehealth application 116 may be tailored to the specific device(s) used by the patient 106. Further, the telehealth application 116 includes various applications that operate on the patient's mobile devices to provide healthcare services.

Also depicted within the home domain 102 is a remote healthcare gateway (RHG) 118. The RHG 118 instantiates a version of a patient's Sealthie, and updates the version of the Sealthie. The RHG 118 is responsible for managing all the data generated by the COTS devices and/or SW applications 110, which data is used by the RHG to update the Sealthie. The RHG 118 also provides an interface between the Sealthie and various SW applications 120 in the Cloud domain 104.

In various embodiments, the RHG 118 may be a stand-alone computing device that is temporarily or permanently installed in a patient's home. In these stand-alone embodiments, the RHG 118 includes a processor, memory, network interface component, and/or wireless transceiver. In other embodiments, the RHG 118 is software implemented on a patient mobile device 122, such as a downloadable application. In still other embodiments, the RHG 118 includes an add-on device, such as a USB dongle, operating in combination with an existing computing device in the home domain 102, i.e., the patient mobile device 122 or a stationary desktop computer. Thus, the RHG 118 may be software executed on a mobile computing device, such as a smartphone.

The patient 106 may run applications on a mobile device 122, which operate as the user interface to the RHG 118. The mobile device 122, may include personal patient devices, such as tablets, smartphones, laptops, and other wirelessly enabled personal computing devices. In an alternative embodiment, the RHG 118 and patient applications 116 are instantiated on a single mobile device instead two separate mobile devices. In this alternative embodiment, the RHG 118 and patient applications 116 are integrated into a single patient application operating on the patient mobile device 122.

The cloud domain 104 represents an internet domain and a collection of servers and applications existing in that domain. As such, the cloud domain 104 is communicatively coupled to the home domain 102 over the Internet or wide area network (WAN). The cloud domain 104 includes various components that are used for existing telehealth services, as well as remote patient monitoring services. More particularly, the cloud domain 104 includes healthcare organization systems 124, a telehealth platform provider 126, medical device vendor servers 128, third-party security provider(s) 130, and the RHG management server 132. Thus, the RHG 118 and/or the mobile device operating the RHG 118 may be communicatively coupled to the one or more components 124-132 of the cloud domain 104 through the WAN. The healthcare organization systems 124, a telehealth platform provider 126, medical device vendor servers 128, and other remote server systems or cloud-based applications, which may generally referred to as third-party cloud components.

The care provider systems 124 include a variety of healthcare servers, such as an Electronic Health Record (EHR), Healthcare Analytics Platforms, Research Institution platforms, and Health Information Exchanges (HIE). Currently, these entities exist within the healthcare industry and exchange information using a variety of standards including a Fast Healthcare Interoperability Resources (FHIR). Healthcare providers generally use these systems to provide services to their patients.

The telehealth platform provider 126 utilizes servers specifically designed to provide telehealth services. These specially designed servers include functions, such as patient video services and manage information from the medical devices 112 and 114 in the home domain 102.

The medical device vendor servers 128 are specific to each vendor of one or more medical device in the home domain 102. Each vendor utilizes a medical device vendor server 128 to manage the one or more corresponding medical device 112, 114 in various patient's home domains 102. The medical device vendor servers 128 collect information, such as diagnostic data and biometric data from the medical devices 112, 114 to ensure proper operation of distributed medical devices 112, 114.

The third-party security provider system(s) 130 are servers that provide Internet security services such as certificates that are used to secure websites and servers (i.e., 128 and 132) on the Internet.

The RHG management server 132 manages the collection of biometric data from the RHG 118 in the home domain 102. In some embodiments, the RHG management server 132 is a cloud component.

Figure 2:
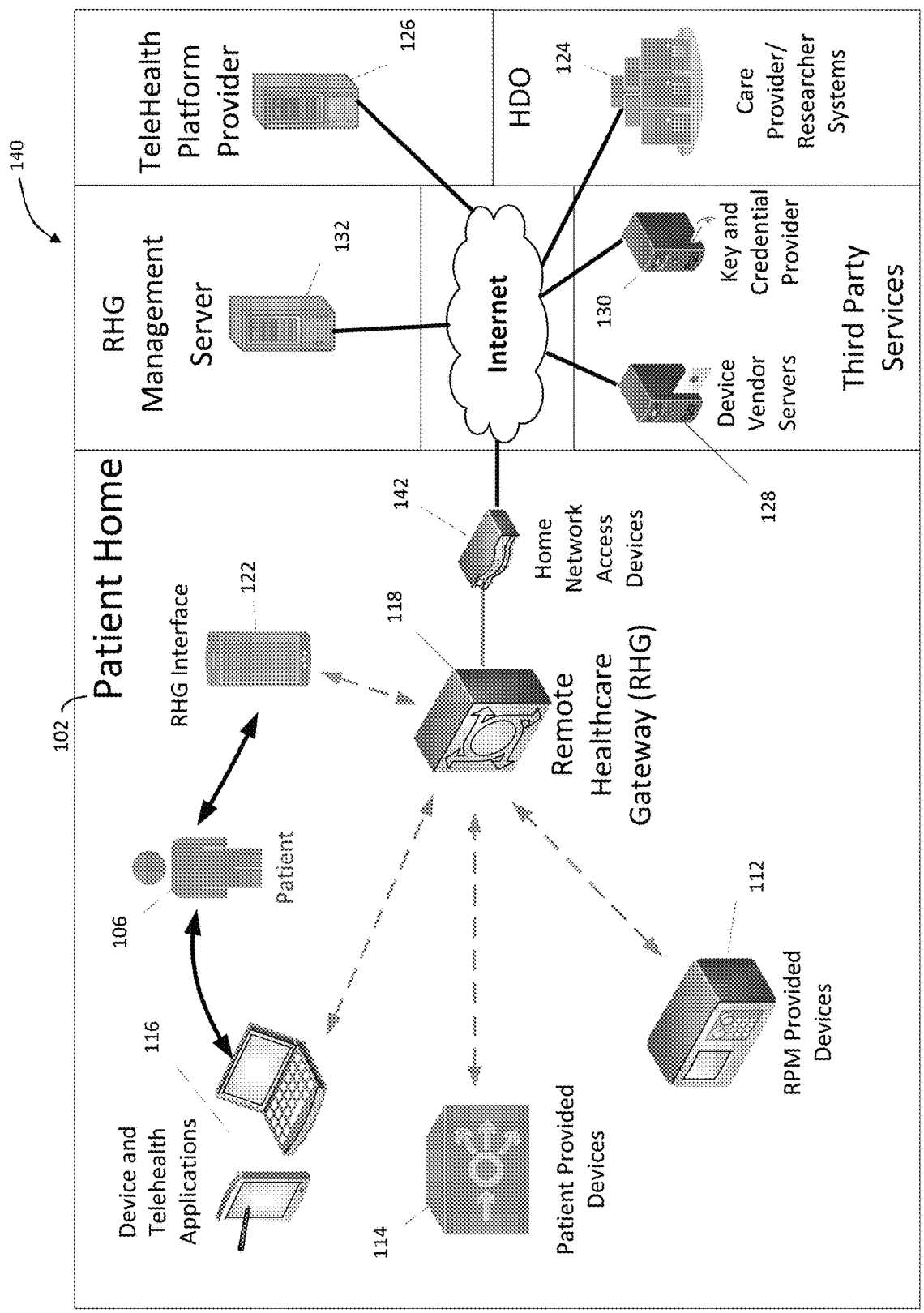
FIG. 2 shows an illustrative communications architecture for the RPM system.

Referring now to FIG. 2, there is shown an illustrative communications architecture 140 for the RPM system, and demonstrates how the RHG 118 operates as a central communications hub for the various components within the home domain 102. The RHG 118 communicates with all of the home domain devices/applications (e.g., 112, 114, 116), as well as the patient mobile device 122 or a particular application operating thereon. In so doing, the RHG 118 instantiates and updates the patient's Sealthie. Further, the RHG 118 provides a communications interface between the home domain devices/applications (e.g., 112, 114, 116, 122) and the various applications (124, 126, 128, 130, 132) in the cloud domain 104.

The various components within the home domain 102 are communicatively coupled over a home network, such as a Local Area Network (LAN), Wi-Fi, Bluetooth, and other such networking protocols. This home network facilitates communications among the various components of within the home domain and communications of those components with the RHG 118. The home network may not exclusively serve the components of the home domain 102, but may instead facilitate communications for other applications, such as home automation, Internet access, or video services, and may be established with standard COTS networking equipment, such as a router 142. In the illustrative embodiment, the home network provides a connection to the Internet for the components with in the home domain 102 using standard Internet or broadband communications technologies.

In the illustrative embodiment, the RHG 118 is an embedded computer with a variety communications interfaces. The RHG 118 may be implemented using a variety of commonly existing computing technologies and embedded operating systems, e.g. Linux.

The RHG management server 132 may be implemented as a cloud server or virtual server, and may operate within a commercial hosting environment. The RHG management server 132 is secured with readily available techniques, which may be provided through the third-party security provider(s) 130.

Figure 3:
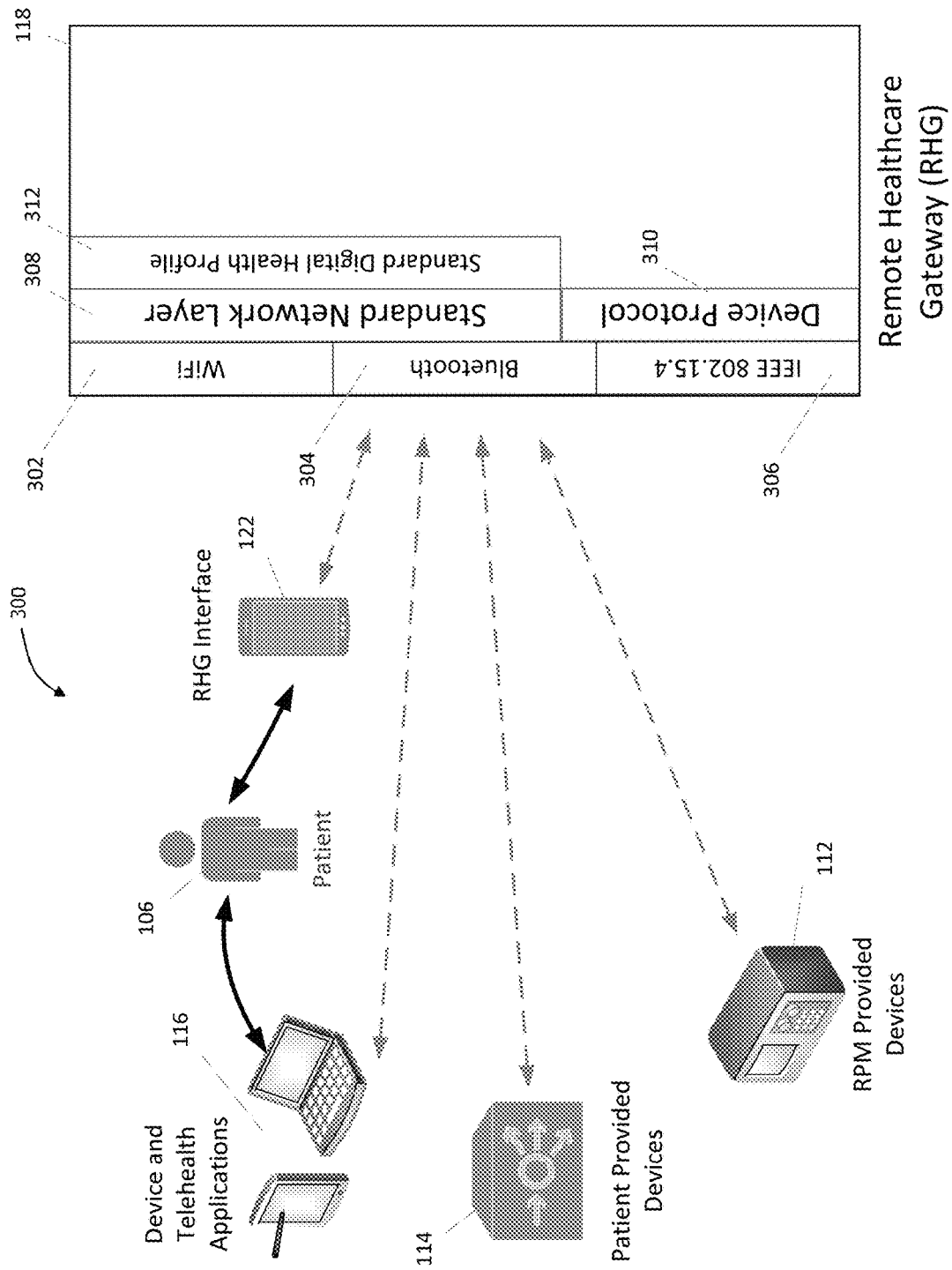
FIG. 3 shows the communication interfaces for a Remote Healthcare Gateway (RHG) in a home domain.

Referring now to FIG. 3, there is shown the communications interfaces 300 of the RHG 118 in the home domain 102. The RHG 118 is configured to communicate with a wide range of COTS medical devices through a plethora of communications interfaces. Generally, the communications interfaces support the receipt of data from the medical devices 112 and 114, monitoring the health and behavior of the medical devices 112 and 114, configuring the medical devices 112 and 114, sending necessary operational commands to the medical devices 112 and 114, performing software updates and maintenance for the medical devices 112 and 114, and supporting patient interfaces with the RHG 118 through mobile devices 122.

The RHG 118 includes physical communications interfaces to the components in the home domain 102, such as Wi-Fi 302, Bluetooth 304, and IEEE 802.15.4 306, or any other commonly available wireless communications technology. Additionally, the RHG 118 uses available home networking technologies to interface with the components of the home domain 102, such as Connected Home over IP (CHIP) 308 or other proprietary communications protocols 310. One of ordinary skill in the art would recognize that other protocols may be used to support existing COTS devices.

In addition to interfacing with the components of the home domain 102, the RHG 118 utilizes a variety of application data models specific to one or more medical device 112 and 114. The medical devices 112 and 114 use these application data models to format the data they each collect and create semantic meaning therefrom. Exemplary application data models include Dotdot used by CHIP 308, Continua, and other similar application data models. Since the RHG 118 interfaces with medical devices 112 and 114 through this broad variety of application data models, the RHG 118 is capable of communicating, exchanging, and interpreting information with and from a wide range of COTS devices that may be implemented in the home domain 102. This breadth of interfacing capability is critical for the RHG's 118 interoperability with the possible medical devices 112 provided to patients, as well as the patient provided medical devices 114.

A standard digital health profile 312 is associated with the RHG 118.

Figure 4:
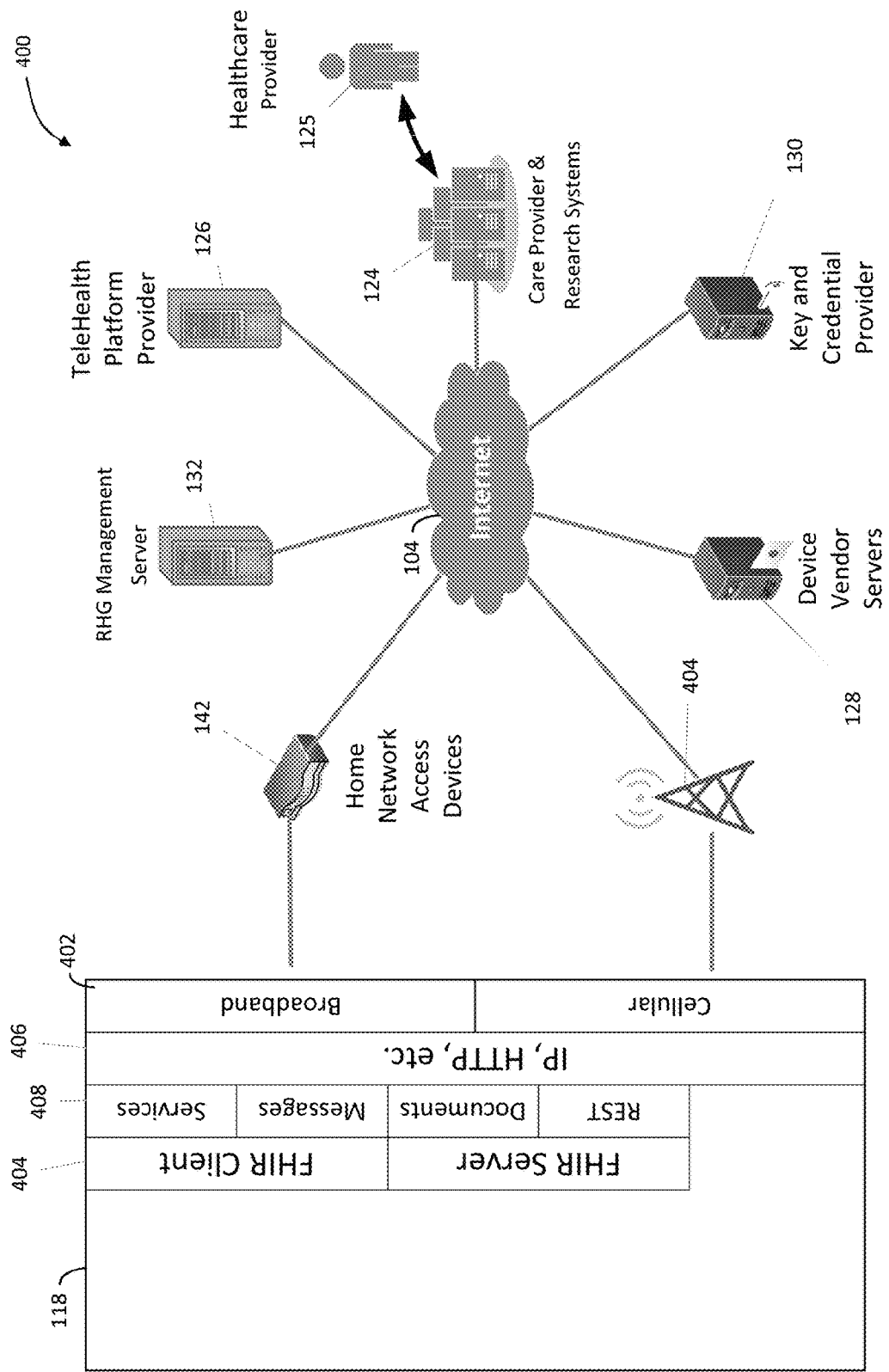
FIG. 4 shows the communication interfaces for a RHG in a cloud domain.

With reference now to FIG. 4, there is shown the cloud domain communication interfaces 400 for the RHG 118. In addition to being the communications hub for the home domain 102, the RHG 118 is also the communications hub between the home domain 102 and the healthcare enterprise applications in the cloud domain 104. In this embodiment, the cloud domain 104 is synonymous with the Internet, and the RHG 118 correspondingly supports a common set of technologies used for Internet-based applications.

In the illustrative embodiment, the common set of technologies supported by the RHG 118 provide access to the data collected by the medical devices 112 and 114 in the home domain 102 through the Sealthie. In this embodiment, the Sealthie operates as a model for the collected data, placing such data in a form that is most conducive to the appropriate healthcare applications (i.e., 124, 126, 128, 132) in the cloud domain 104, and improving a healthcare provider's 125 access to such data. The interfaces to the cloud-based applications may provide a portal for the cloud-based applications to the Sealthie instantiated within the RHG 118.

In other embodiments, the interfaces to the cloud-based applications provide raw data feeds from the medical devices 112 and 114 in the home domain 102. In all embodiments, the interfaces to the cloud-based applications may receive configuration information for the medical devices 112 and 114 in the home domain 102. This configuration information includes software updates from the respective vendors of each of the medical devices 112 and 114 in the home domain 102. Additionally, the interfaces to the cloud-based applications may receive patient information from other sources.

At the physical layer, the RHG 118 interfaces to commonly available home networking equipment 142 (e.g., router, modem, or other Internet access point). These interfaces may be embedded in the RHG 118. The commonly available home networking equipment may exist in the home domain for purposes other than healthcare, such as entertainment, professional, or other non-healthcare purposes. The home networking equipment 142 typically constitutes a broadband Internet connection 402 provided by an Internet Service Provider (ISP). The RHG 118 may also or alternatively interface to the Internet through a cellular network connection 404. All of the RHG interfaces utilize commonly available technologies that may be easily embedded into the RHG 118 by one of ordinary skill in the art.

In order to readily interface with Internet-based applications, the RHG 118 supports all typical networking protocols deployed by such Internet-based applications, including IP, HTTP, etc. 406. These networking protocols may be embedded in the RHG 118. Additionally, the RHG 118 supports implementation of a suite of standard Internet-based data exchange methodologies 408, such as REST, Document exchange, Messages, and Services. In all cases, the networking protocols and interaction categories are readily embedded and implemented in the RHG 118 using well known methodologies by those of ordinary skill in the art. Further still, the RHG 118 supports standard methodologies specific to the healthcare industry, such as FHIR, which facilitate the standardized exchange of healthcare-specific information between the medical devices 112 and 114 in the home domain 102 and the cloud-based healthcare applications (i.e., 124, 126, 128, 132).

Figure 5A:
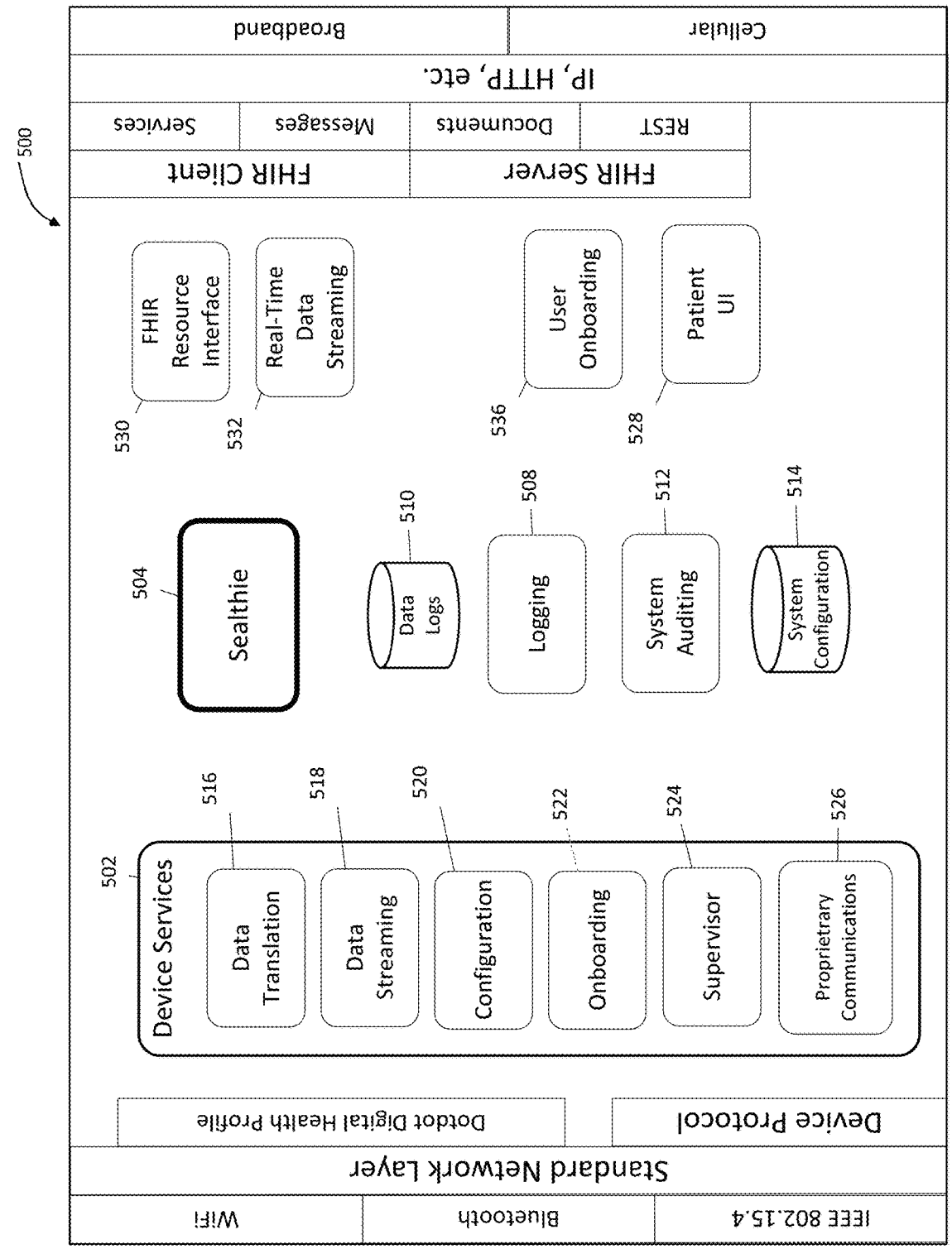
FIG. 5A shows a block diagram of an illustrative RHG.

Referring now to FIG. 5A, there is shown a block diagram of the RHG software components and functions 500. The RHG 118 includes three (3) data structures corresponding to three (3) core operations, a suite of medical device services 502, and an assortment of external interfacing functions. The three (3) data structures and corresponding three (3) core operations are the Sealthie 504, which is both a core operation and a data structure, RHG logging 508, data logs 510, RHG auditing 512, and an RHG configuration database 514. The suite of medical device services 502 includes data translation 516, data streaming 518, configuration 520, onboarding 522, supervisor 524, and proprietary communications 526.

The Sealthie 504 is a self-contained software module having a database containing attributes for each patient 106 and one or more routines facilitating the receipt of data from medical devices 112 and 114, the cloud applications 124, 126, 128, 132, and other sources. As an independent software module, the Sealthie 504 is a transportable module that is not limited to instantiation on the RHG 118, but instead is only represented here in the RHG 118 as an exemplary instantiation of the Sealthie 504.

The Sealthie 504 also updates the state of the patient stored in the Sealthie 504. This operation translates the received data from the models used by the various home domain components, i.e. medical devices so that the received data can be stored in the Sealthie 504.

In particular, the Sealthie 504 includes patient profiles, the current state of data elements measured by various medical devices 112 and 114, historical health data measured by the various medical devices 112 and 114, and miscellaneous health and wellness records obtained from other sources. Together, these elements stored in the Sealthie 504 are generally referred to as patient healthcare data items that include provider health records, electronic health records, genomic data, exomic data, medical device readings, medical device reports, a list of patient allergies, an inventory of patient medications, pharmacy number, prescriber, strength, dosage, purpose, side effects, drug-drug interactions, indications to alert clinicians to reactions, quantity remaining, timing for refills, questionnaire responses, and transaction logs.

The patient profiles may further include access and security policies specific to each patient.

The RHG 118 provides a separate suite of medical device services 502 for each medical device 112 or 114. The suite of services 502 are tailored for each specific medical device type. In some embodiments, each unique suite of services 502 are downloaded to the RHG 118.

Within the suite of medical device services 502, the data translation service 516 enable the RHG 118 to receive data from various home domain components using a protocol or data model specific to the particular component, by translating the received data into a common model. Once translated, the common model data is saved in the Sealthie.

In some embodiments, the data collected from the home domain components is streamed in real time through the RHG 118 to one or more healthcare applications (124, 126, 128, 130, 132) in the cloud domain 104. The data streaming service 518 manages the streams of home domain component data and converts the collected data from the data model used by the particular medical device 112 and 114 to a form suitable for the receiving cloud application. In some embodiments, the collected data is stored, then forwarded in a bulk format at a future time.

The data streaming service 518 pairs with a real-time data streaming operation 532 that transfers the streamed data from the RGH 118 to the cloud-based healthcare applications 124-132. This process manages the data streams and ensures that the data is sent appropriately.

The configuration service 520 manages the configuration of the RHG 118. The configuration of the RHG 118 is stored in the RHG configuration database 514. The RHG configuration information may include miscellaneous RHG configuration parameters, configurations of the home domain components that are managed by the RHG 118, security parameters and configurations, and mapping data that defines how data collected from the home domain components is converted and transmitted to the cloud applications (124, 126, 128, 130 132).

The onboarding service 522 manages the process of deploying the various medical devices 112 and 114 and establishing a connection between the RHG 118 and the medical devices 112 and 114 according to the device configurations defined by the configuration service 520 and stored in the configuration database 514.

The supervisor service 524 monitors the operations of the various medical devices 112 and 114 and determines whether those devices are operating properly. In some embodiments, the supervisor service 524 detects security flaws and/or problems.

The proprietary communications service 526 allows the RHG 118 to implement one or more proprietary protocols to support communications with a medical device 112 or 114 that operates with a corresponding proprietary protocol. Although, the RHG 118 typically uses standard home automation protocols.

The RHG 118 presents a user interface 528 to patients 106, through which patients access the RHG on their mobile devices 122. The patient interface 528 allows patients 106 to monitor and manage the RHG, such as configuring access and security policies stored in the Sealthie database 506.

The RHG 118 includes a system auditing process 512 that operates to monitor the efficacy and overall "health" of the RHG 118. The auditing process 512 detects security flaws and/or incursions, then logs any anomalies detected.

The RHG 118 exchanges information with the cloud-based healthcare applications 124-132 using standardized methods. One such method is FHIR, the configuration for how information from the home domain components is mapped to the FHIR interfaces are stored in the RHG configuration database 514.

Patient onboarding 536 is enabled through an RHG interface that allows patients 106 to be associated with the RHG 118, and allows the RHG 118 to be installed and configured. Patient onboarding 536 includes associating the Sealthie with the RHG 118.

The RHG 118 performs data logging 508 where it logs its activity, including its interaction with the home domain components and cloud-based applications, into a data log 510.

Figure 5B:
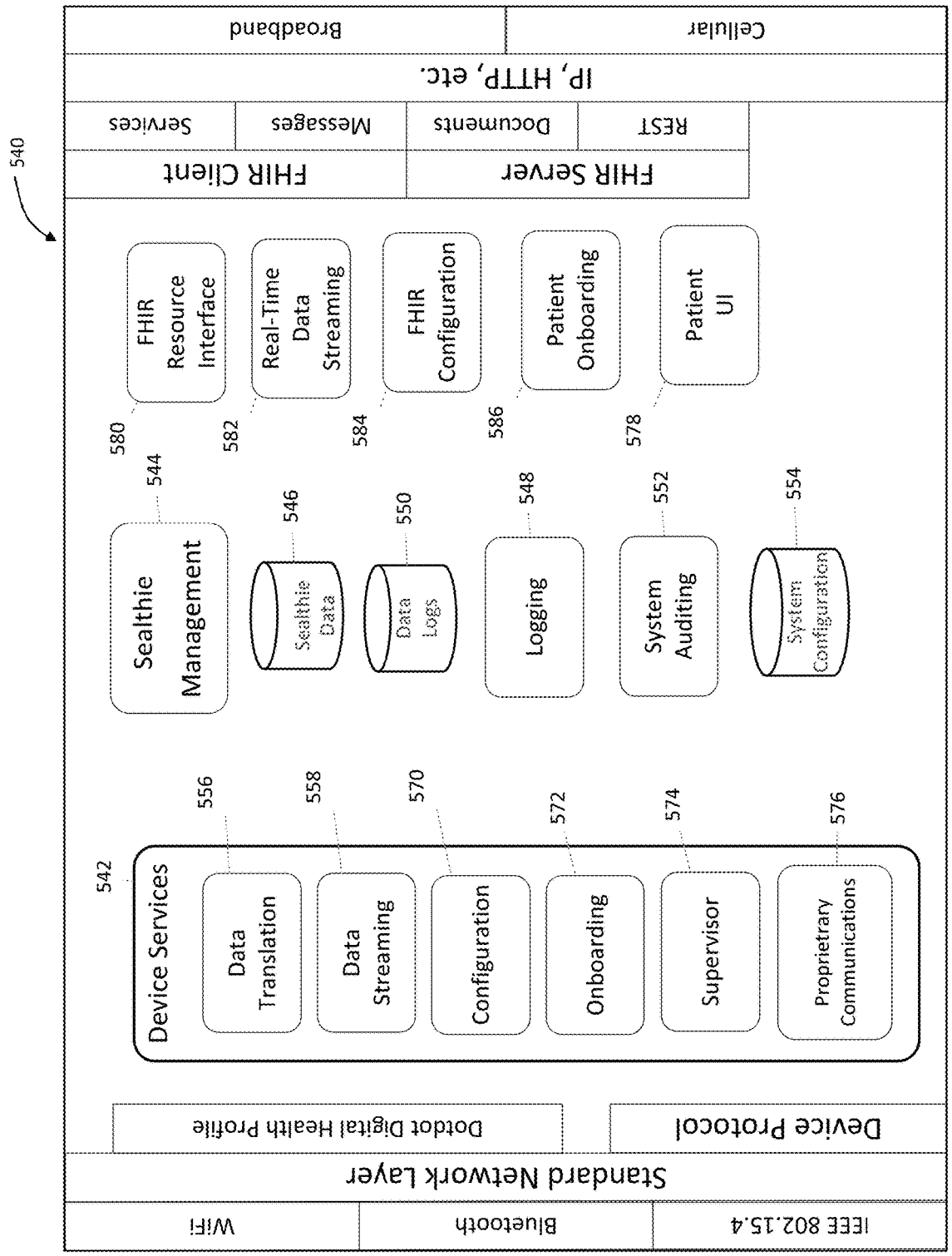
FIG. 5B shows a block diagram of an alternate RHG.

Referring now to FIG. 5B, there is shown a block diagram 540 of software components and functions for an alternate RHG configuration. The RHG 118 includes three (3) data structures corresponding to three (3) core operations, a suite of medical device services 542, and an assortment of external interfacing functions. The three (3) data structures and corresponding three (3) core operations are the Sealthie management operation 544, the Sealthie data structure 546, RHG logging 548, data logs 550, RHG auditing 552, and an RHG configuration database 554. The suite of medical device services 542 includes data translation 556, data streaming 558, configuration 570, onboarding 572, supervisor 574, and proprietary communications 526.

The Sealthie data structure 546 is a database containing attributes for each patient 106. In particular, the Sealthie database 546 includes patient profiles, the current state of data elements measured by various medical devices 112 and 114, historical health data measured by the various medical devices 112 and 114, and miscellaneous health and wellness records obtained from other sources. Together, these elements stored in the Sealthie database 546 are generally referred to as patient healthcare data items that include provider health records, electronic health records, genomic data, exomic data, medical device readings, medical device reports, a list of patient allergies, an inventory of patient medications, pharmacy number, prescriber, strength, dosage, purpose, side effects, drug-drug interactions, indications to alert clinicians to reactions, quantity remaining, timing for refills, questionnaire responses, and transaction logs.

The patient profiles may further include access and security policies specific to each patient.

The Sealthie management operation 544 receives data from medical devices 112 and 114, the cloud applications 124, 126, 128, 132, and other sources, and updates the state of the patient Sealthie stored in the Sealthie data structure 546. This operation 544 translates the received data from the models used by the various home domain components, i.e., medical devices so that the received data can be stored in the Sealthie data structure 546.

The RHG 118 provides a separate suite of medical device services 542 for each medical device 112 or 114. The suite of services 542 are tailored for each specific medical device type. In some embodiments, each unique suite of services 542 are downloaded to the RHG 118.

Within the suite of medical device services 542, the data translation service 556 enable the RHG 118 to receive data from various home domain components using a protocol or data model specific to the particular component, by translating the received data into a common model. Once translated, the common model data is saved in the Sealthie.

In some embodiments, the data collected from the home domain components is streamed in real time through the RHG 118 to one or more healthcare applications (124, 126, 128, 130, 132) in the cloud domain 104. The data streaming service 558 manages the streams of home domain component data and converts the collected data from the data model used by the particular medical device 112 and 114 to a form suitable for the receiving cloud application. In some embodiments, the collected data is stored, then forwarded in a bulk format at a future time.

The data streaming service 558 pairs with a real-time data streaming operation 582 that transfers the streamed data from the RGH 118 to the cloud-based healthcare applications 124-132. This process manages the data streams and ensures that the data is sent appropriately.

The configuration service 570 manages the configuration of the RHG 118. The configuration of the RHG 118 is stored in the RHG configuration database 554. The RHG configuration information may include miscellaneous RHG configuration parameters, configurations of the home domain components that are managed by the RHG 118, security parameters and configurations, and mapping data that defines how data collected from the home domain components is converted and transmitted to the cloud applications (124, 126, 128, 130 132).

The onboarding service 572 manages the process of deploying the various medical devices 112 and 114 and establishing a connection between the RHG 118 and the medical devices 112 and 114 according to the device configurations defined by the configuration service 570 and stored in the configuration database 514.

The supervisor service 574 monitors the operations of the various medical devices 112 and 114 and determines whether those devices are operating properly. In some embodiments, the supervisor service 574 detects security flaws and/or problems.

The proprietary communications service 576 allows the RHG 118 to implement one or more proprietary protocols to support communications with a medical device 112 or 114 that operates with a corresponding proprietary protocol. Although, the RHG 118 typically uses standard home automation protocols.

The RHG 118 presents a user interface 578 to patients 106, through which patients access the RHG on their mobile devices 122. The patient interface 578 allows patients 106 to monitor and manage the RHG, such as configuring access and security policies stored in the Sealthie database 546.

The RHG 118 includes a system auditing process 512 that operates to monitor the efficacy and overall "health" of the RHG 118. The auditing process 512 detects security flaws and/or incursions, then logs any anomalies detected.

The RHG 118 exchanges information with the cloud-based healthcare applications 124-132 using standardized methods. One such method is FHIR, thus the RHG 118 presents an FHIR interface 580 to the cloud-based healthcare applications 124-132. The configuration for how information from the home domain components is mapped to the FHIR interfaces are stored in the RHG configuration database 554. Further, the RHG 118 presents an interface 584 that allows the home domain component to FHIR mapping to be configured into the RHG configuration database Patient onboarding 586 is enabled through an RHG interface that allows patients 106 to be associated with the RHG 118 and allows the RHG 118 to be installed and configured. Patient onboarding 586 includes associating the Sealthie with the RHG 118.

The RHG 118 performs data logging 548 where it logs its activity, including its interaction with the home domain components and cloud-based applications, into a data log 550.

Figure 6:
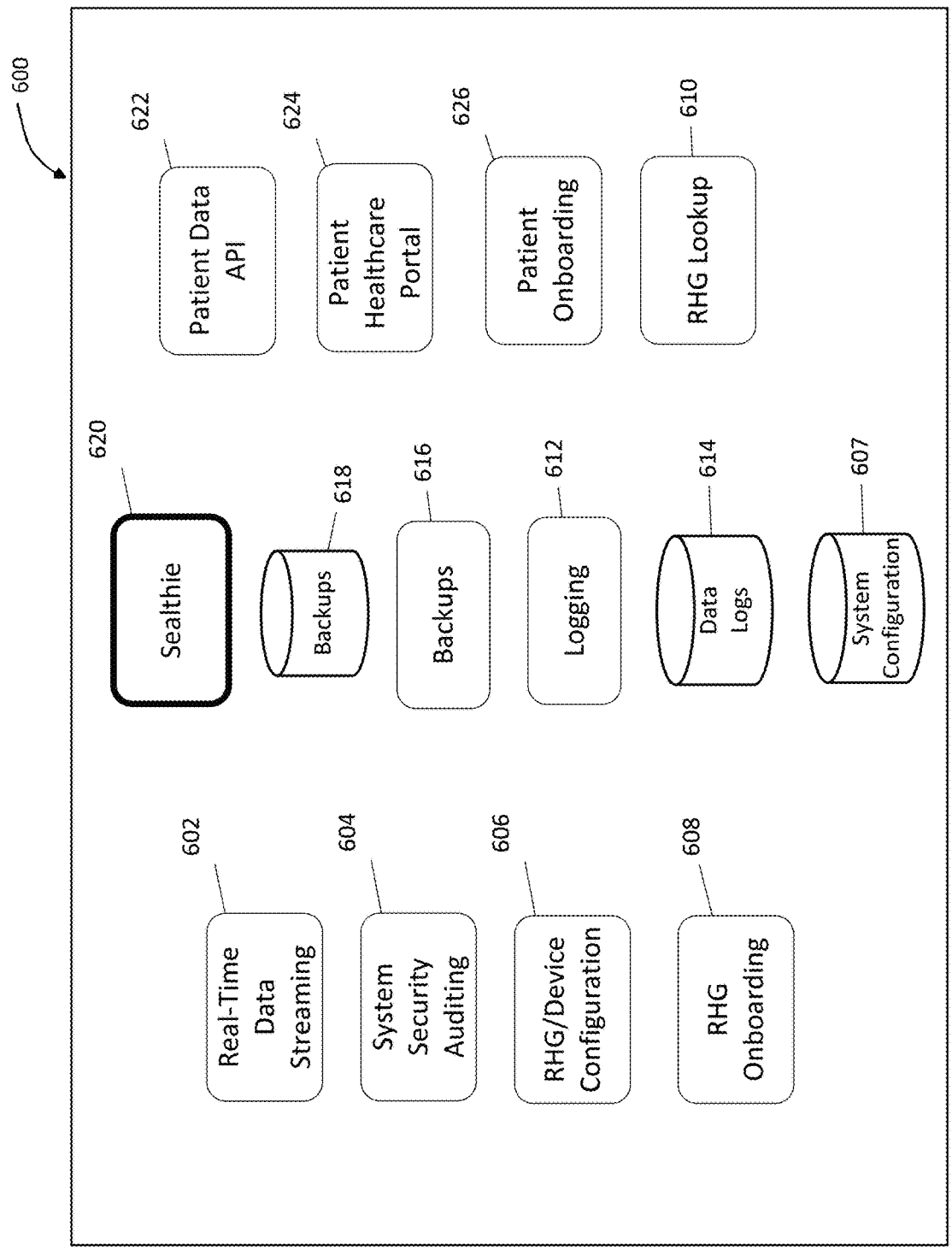
FIG. 6 shows a block diagram for an illustrative RHG cloud server.

With reference now to FIG. 6, there is shown a block diagram 600 for an illustrative RHG cloud server 132. Generally, the RHG management server 132 mirrors the functionality of the RHG 118, including an instantiation of each patient's Sealthie. This allows the functionality of the Sealthie to be instantiated in either the RHG 118 or the cloud-based RHG management server 132. This also enables the patients' Sealthies to be backed up in the cloud (i.e., RHG management server 132).

As with the RHG data streaming service 518, the RHG management server data streaming service 602 manages the streams of home domain component data and converts the collected data from the data model used by the particular medical device 112 or 114 to a form suitable for other cloud applications. More generally, the RHG management server 132 operates as a proxy data streamer for the RHG 118.

The RHG management server 132 includes a system security auditing function 604 that audits the security of the RHG management server 132, as well as the security of all the RHGs 118 communicatively coupled to the RHG management server 132.

The RHG management server 132 includes a configuration process 606 for the configuration of both RHGs 118 and medical devices. These configurations are then stored in a database 607 that stores the configuration of each medical device and each RHG 118.

The RHG management server 132 includes an RHG onboarding portal 608 that is presented to patients and various third-parties. The RHG onboarding portal 608 allows the installation and configuration of home domain medical devices 112 and 114 during the initial configuration of each RHG 118 connected to the RHG management server 132.

The RHG management server 132 includes an RHG lookup function 610 that enables other cloud-based applications to locate RHGs 118 and Sealthies based on patient identification information.

The RHG management server 132 includes a logging function 612 that logs the various transactions with RHGs 118 and other systems in a data logs database 614 resident on the RHG management server 132.

The RHG management server 132 includes a backup function 616 that stores a backup copy of the information on each RHG 118 in a backup database 618 resident on the RHG management server 132. Additionally, or alternatively, the RHG management server 132 stores a backup copy of the information on each RHG 118 as a separate instantiation of the patient Sealthie 620. In some embodiments, the RHG management server 132 includes a patient data application programming interface (API) 622 through which patients may access the data in their Sealthies 620. In these embodiments, the RHG management server 132 operates as a proxy for the RHG 118 with respect to accessing patient data stored in their Sealthie 620.

The RHG management server 132 presents a browser-based patient healthcare/wellness portal 624 for each patient to access their Sealthie 620, view their Sealthie information, and configure access to their Sealthie 620. Through the healthcare/wellness portal 624, the RHG management server 132 may generate health-related tasks for patients to address or perform. These tasks are based upon the data items in the patient's Sealthie 620 and may include an instruction to take medication, an instruction to attend an appointment, and other such data items. Additionally, the RHG management server 132 may generate a plurality of task alerts, a plurality of security alerts, a plurality of message alerts, and a plurality of device alerts that can be distributed to the patient through the healthcare/wellness portal 624. In an alternative embodiment, the health-related tasks, task alerts, security alerts, message alerts, and device alerts may be delivered from the RHG management server 132 over the Internet to the RHG mobile application and thereby the patient 106.

The RHG management server 132 may also enable patient onboarding 626 through the browser-based patient healthcare portal 624, or through a web-based API. This onboarding process 626 includes the creation of patient profiles (or accounts) and corresponding Sealthies 620.

Figure 7:
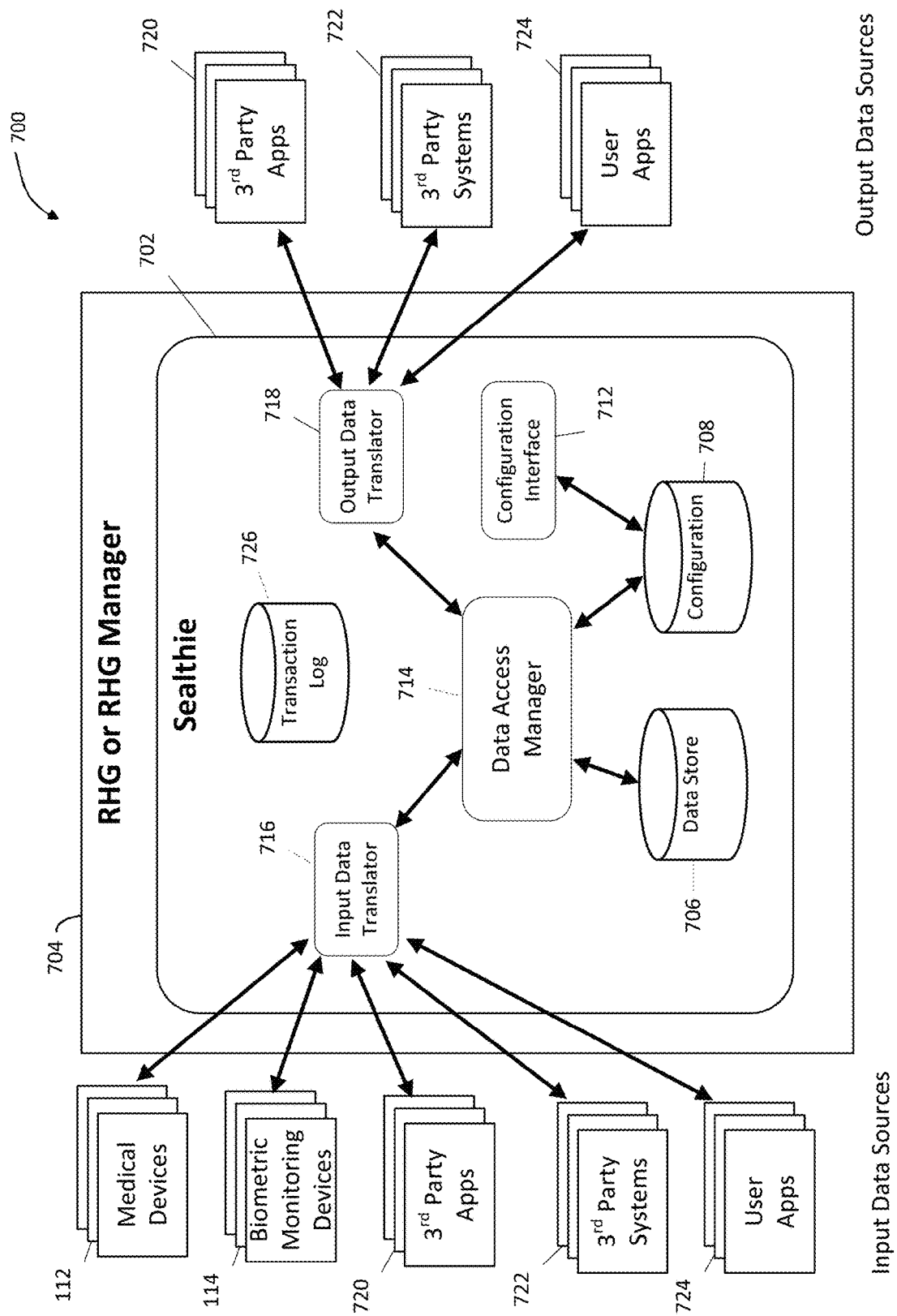
FIG. 7 shows an illustrative block diagram of a Sealthie application.

With reference now to FIG. 7, there is shown an illustrative block diagram 700 of a Sealthie application 702 instantiated on a computing device 704 representing the mobile device 122 operating the RHG 118, a stand-alone RHG 118, the RHG Management server 132, or any combination thereof. The Sealthie 702 is an independent, modular software application and data structure, allowing for easy backup and transportation between systems, servers, and/or computing devices. The Sealthie 702 may be implemented using a variety of programming languages, and deployed on a corresponding variety of platforms/operating systems. Additionally, all instantiations of the Sealthie 702 include interfaces to its functionality that range from linked libraries to message busses.

The Sealthie 702 performs several functions supporting tracking a patient's biometrics, updating a patient's healthcare state, and storing a patient's medical records. The Sealthie 702 models the overall healthcare state of an associated patient 106. The Sealthie 702 stores both present and past healthcare states of each patient 106. The Sealthie 702 stores various healthcare records of each patient 106. The Sealthie 702 receives, processes, and stores healthcare related information from many different types of sources. These sources range from patient provided devices 114 and medical devices 112 that measure health-related information to cloud-based systems that contain health records 124 and 126. The Sealthie 702 provides certain selected patient information to various healthcare applications 124 and 126 upon request by those applications and authorization by the patient 106. The Sealthie 702 configures how information is integrated into the Sealthie 702 itself. These configurations determine both how this information is modeled and what sources of information are accepted by the Sealthie 702. The Sealthie 702 also configures itself to control access to the patient information stored therein.

In the illustrative embodiment, the Sealthie 702 includes a "replicate model" of the patient's health state. The replicate model is developed a data set that is a subset of the Sealthie. Thus, the replicate model includes representations of patient attributes. These attributes may be determined from measured patient biometrics, such as body temperature, heartrate, blood pressure, glucose level, EKG readings, blood oxygen saturation, sleep times, sleep quality, weight, etc.

In general, the replicate model may include any sort of physiological attribute that can be measured from a patient 106. The replicate model is independent of the source of the measurements and not dependent upon specific patient provided devices 114 or medical devices 112 that may take the attribute measurements. In addition to being updated with data from patient provided devices 114 or medical devices 112, the replicate model can also be updated with data from medical records. In some embodiments, the replicate model is updated in the Sealthie 702 using device communication standards, such as IEEE 11073.

The Sealthie 702 may include more information than is represented in the replicate model for a particular patient 106. For example, the Sealthie 702 may store historical records or auxiliary health records from multiple sources, such as care providers 108, healthcare organization systems 124, etc.

In the block diagram 700 the components of the Sealthie 702 and their relationship to one another are depicted. The complete state of the Sealthie 702 is represented in combination by the data store 706, the Sealthie configuration 708, and the transaction logs 710. This relation of functional components in the Sealthie 702 allows for the complete reproduction of the Sealthie 702 by merely saving and copying the data of the data store 706, the Sealthie configuration 708, and the transaction logs 710. Thus, the Sealthie 702 greatly simplifies both backup operations and reproduction of the entire digital health history for any patient.

A data access manager 714 is communicatively coupled to the data store 706 the configuration 708, an input data translator 716 and an output data translator 718. The data access manager 714 controls access to the data store 706. In one embodiment, the data access manager 714 control access by ensuring that data inputs match Sealthie configuration parameters and that the data inputs have permissions relevant to the Sealthie configuration parameters. The data access manager 714 also determines that data requests meet the configuration parameters. This determination may include denying data requests, limiting the data transferred to or displayed in the replicate model, and/or approving data requests. In so doing, the data access manager 714 ensures that data outputs comply with the relevant permissions associated with particular medical records and/or biometric data. This causes the RHG management server 132 or RHG 118 not to distribute instantiations of a patient's replicate model that includes patient data without permission from the patient entered into the Sealthie configuration.

The data store 706 stores instantiations of the replicate model and the auxiliary health and wellness records.

The data access manager 714 integrates data inputs with existing Replicate Model instantiations, reads and writes data to the data store 706, and ensures proper credentials are used to access the data store 706 and/or the instantiations of the Replicate Model by healthcare applications 124, 126, healthcare providers 108, and the patient 106 (i.e., ensures the patient is the patient). The requirement for proper credentials may include encrypting the data store 706 and/or the instantiations of the Replicate Models, which provides HIPAA-compliant security.

The Sealthie configuration 708 includes several system defining selections. One system defining selection of the Sealthie configuration 708 is a selection of the particular attributes of a patient health state that are included in an instantiation of a patient's Sealthie 702, i.e., the replicate model. In some embodiments, the Sealthie configuration 708 is set to include every attribute of a patient health state in an instantiation of the patient's Sealthie 702. Any number of particular attributes of the patient health state may be selected for inclusion in an instantiation of the patient's Sealthie 702, such as a display made available to healthcare provider applications 124 and 126 or made available to a particular healthcare provider 108. Thus, zero, one, or more attributes, up to every attribute may be selected in the Sealthie configuration 708 for inclusion in the instantiation of the patient's Sealthie 702.

The Sealthie configuration 708 includes one or more mappings between various data input sources, i.e., biometrics from medical devices, data from health records, etc., and the patient's replicate model. The Sealthie configuration 708 also includes one or more mappings between various replicate model attributes and various data outputs, i.e., healthcare organization systems 124, telehealth platform providers 126, and healthcare providers 108. To support these mappings, the Sealthie configuration 708 defines the supported data inputs and the supported data outputs.

A configuration interface 712 allows a user to access the Sealthie configuration 708, view definitions, view mappings, and view/modify attribute selections for instantiations of the replicate model. Thus, the configuration interface 712 can be used to both read and write those configuration attributes selected or available for selection.

The input data translator 716 receives input from a range of data sources and translates the received input into a form compatible one or more instantiations of the replicate model. In some embodiments, the input data translator 716 is a software module that interfaces with the data access manager 714 to allow the data access manager 714 to integrate receive input into the data store 706. Data received at the input data translator 716 that is not authorized by the data access manager 714 will not be integrated into instantiations of the replicate model or the data store 706.

The input data translator 716 receives data from remote patient monitoring devices 112, patient provided devices 114, third-party applications 720, third-party systems 722, and user applications 724 (e.g., wellness applications). These remote patient monitoring devices 112 may include any healthcare provided medical devices, such as thermometers, blood pressure cuffs, EKGs, pulse oximeters, stethoscopes, and autoscopes. The patient provided devices 114 may include biometric monitoring devices associated with wellness applications, such as activity monitors and other wearables. The patient provided devices 114 generally do not produce medical grade data and are not generally used for diagnostic purposes. The third-party applications 720 are provided by third-parties and may be used to monitor patient health, medication adherence, scheduling reminders, and health education. The third-party systems 722 are cloud-based enterprise systems 124 that include EHRs, healthcare payer systems, researcher systems, telehealth platforms 126, medical and other biometric monitoring device vendor servers 128, etc. The third-party applications 720 and the third-party systems 722 may collectively be referred to as third-party cloud components. The user applications 724 include health and wellness applications used by individuals on personal computing devices, such as the patient mobile device 122.

The output data translator 718 transfers data from the Replicate Model in the data store 706 to various output sources. The output data translator 718 translates data from the Replicate Model to one or more formats (i.e., HL7 or FHIR) necessary for the receiving system or the output system. The output data translator 718 allows the Sealthie 702 to make patient data available to the third-party applications 720, the third-party systems 722, and the user applications 724.

The Sealthie 702 also includes a transaction log 726 containing records of all transactions with the Sealthie. The transaction log 726 also includes an interface for accessing the records stored thereon.

Figure 8:
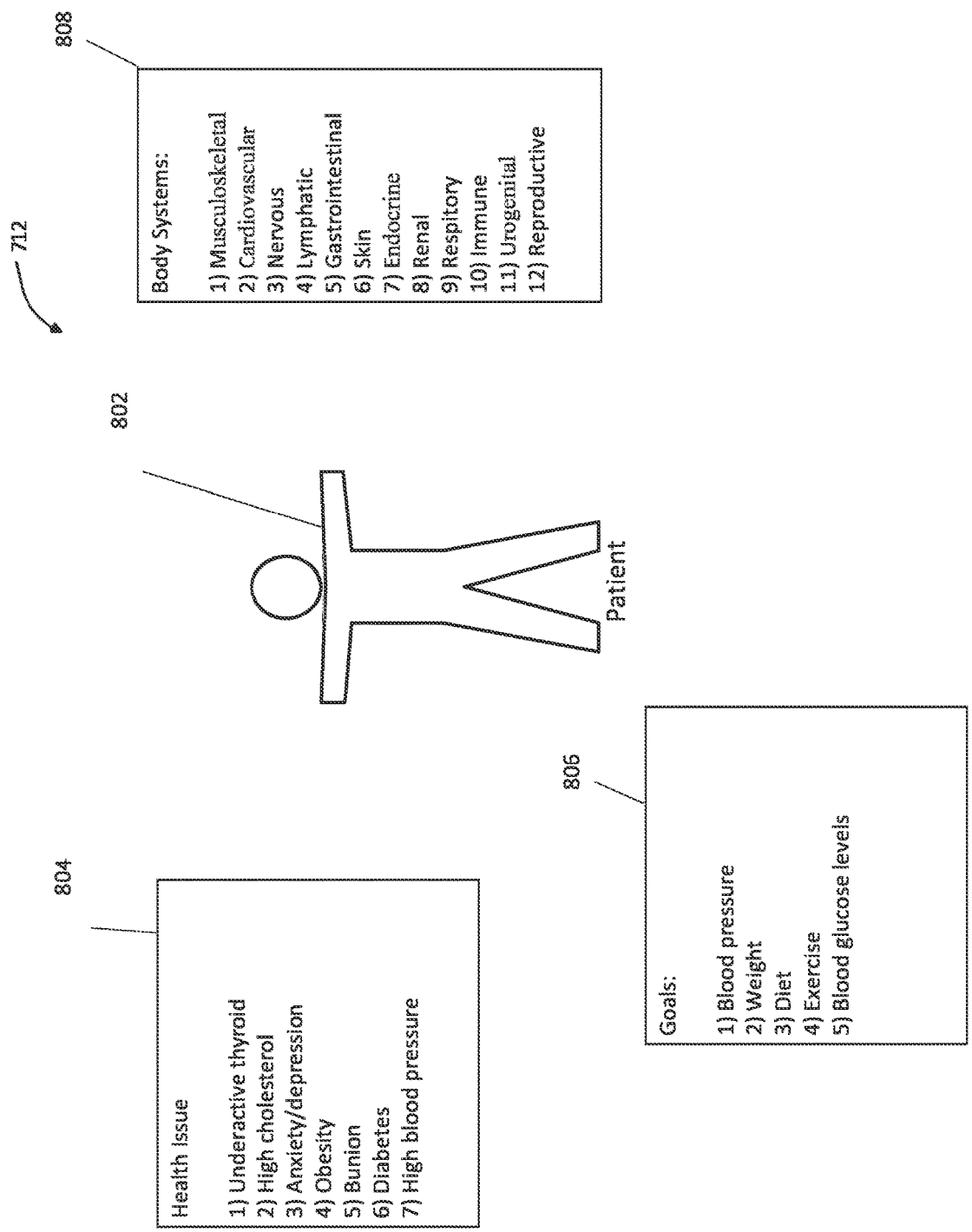
FIG. 8 shows an illustrative Sealthie configuration interface.

Referring now to FIG. 8, there is shown an exemplary embodiment of the configuration interface 712. In this embodiment, the patient replicate model may be displayed as an avatar representation 802 with three menus having information and selection which determine the information presented in the avatar representation 802, a health issue menu 804, a goal menu 806, and body system menu 808.

The health issue menu 804 provides patients with a consolidated view of a problem lists from their healthcare providers' electronic EHRs, which are presented as issues listed in the health issue menu 804, such as underactive thyroid, high cholesterol, anxiety, depression, obesity, bunion, diabetes, high blood pressure, etc. Patients can select one or more issues from the health issue menu 804 to view details and suggested activities. The goal menu 806 provides a high-level view of health goals in a list. Patients can select one or more health goals from the goal menu 806 to view details and suggested activities. The body system menu 808 provides patients an anatomy education on each major physiological systems through menu items including cardiovascular, gastrointestinal, endocrine, musculoskeletal, nervous, renal, respiratory, immune, lymphatic, urogenital, skin, reproductive, etc. This anatomy and physiology information allows patients to visualize and understand the relationships between their healthcare issues, goals, and related specialty care.

Figure 9:
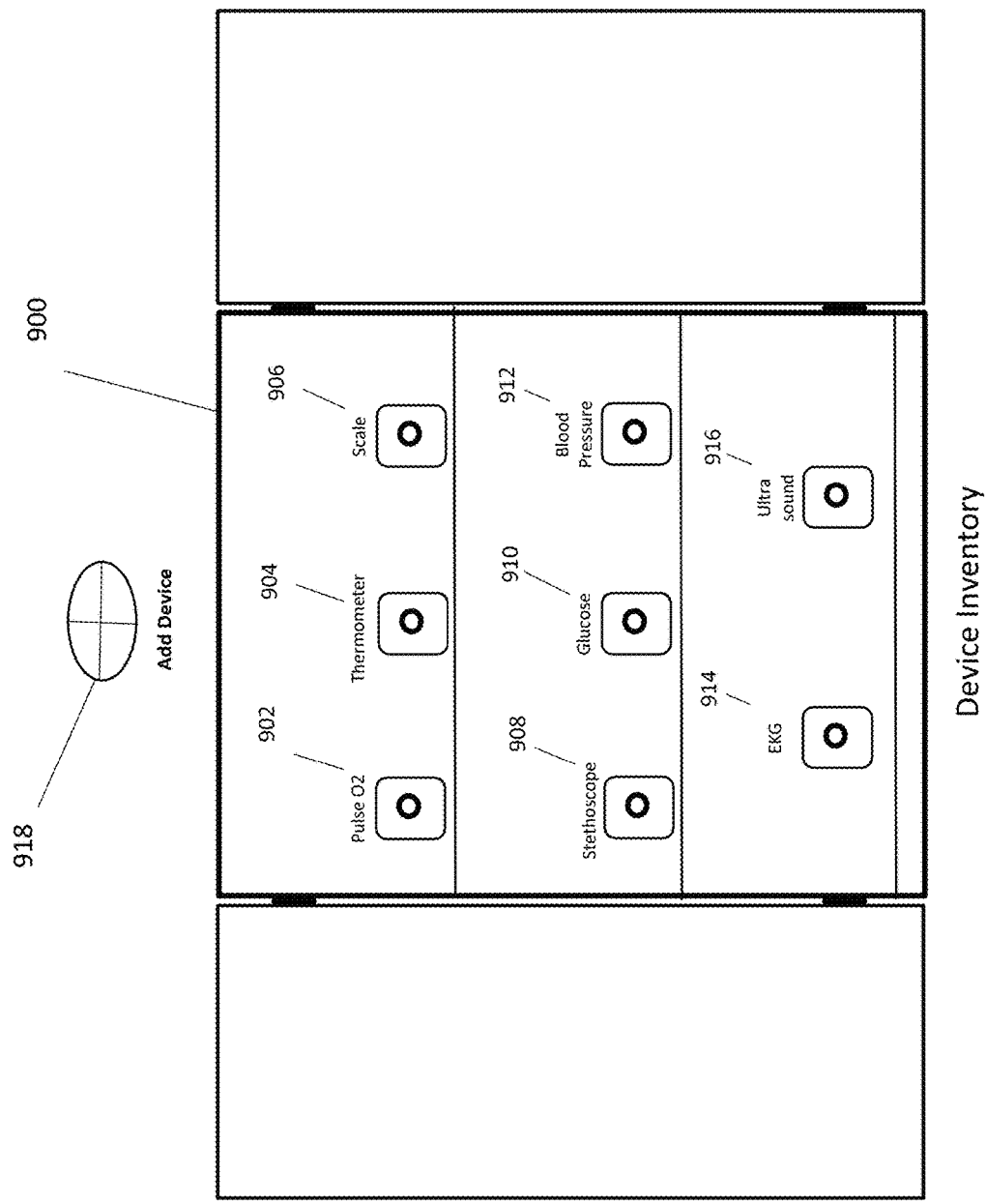
FIG. 9 shows an illustrative menu within the Sealthie configuration interface.

With reference now to FIG. 9, there is shown another exemplary menu 900 of the configuration interface 712. This exemplary configuration interface menu 900 is a device inventory presented to patients to allow them to view, add, or remove medical devices 112, patient provided devices and other wearables 114, or any device used for recording biometric data and images, participating in telehealth examinations, and treating patient medical conditions. As described variously herein, these devices include pulse oximeters 902, thermometers 904, scales 906, stethoscopes 908, glucose monitors 910, blood pressure monitors 912, EKG monitors 914, ultrasound machines 916, skin analysis machines, autoscopes, orthopedic corrective therapy devices, or wellness devices. An add device icon 918 presents patients with a device management interface 1000.

Figure 10:
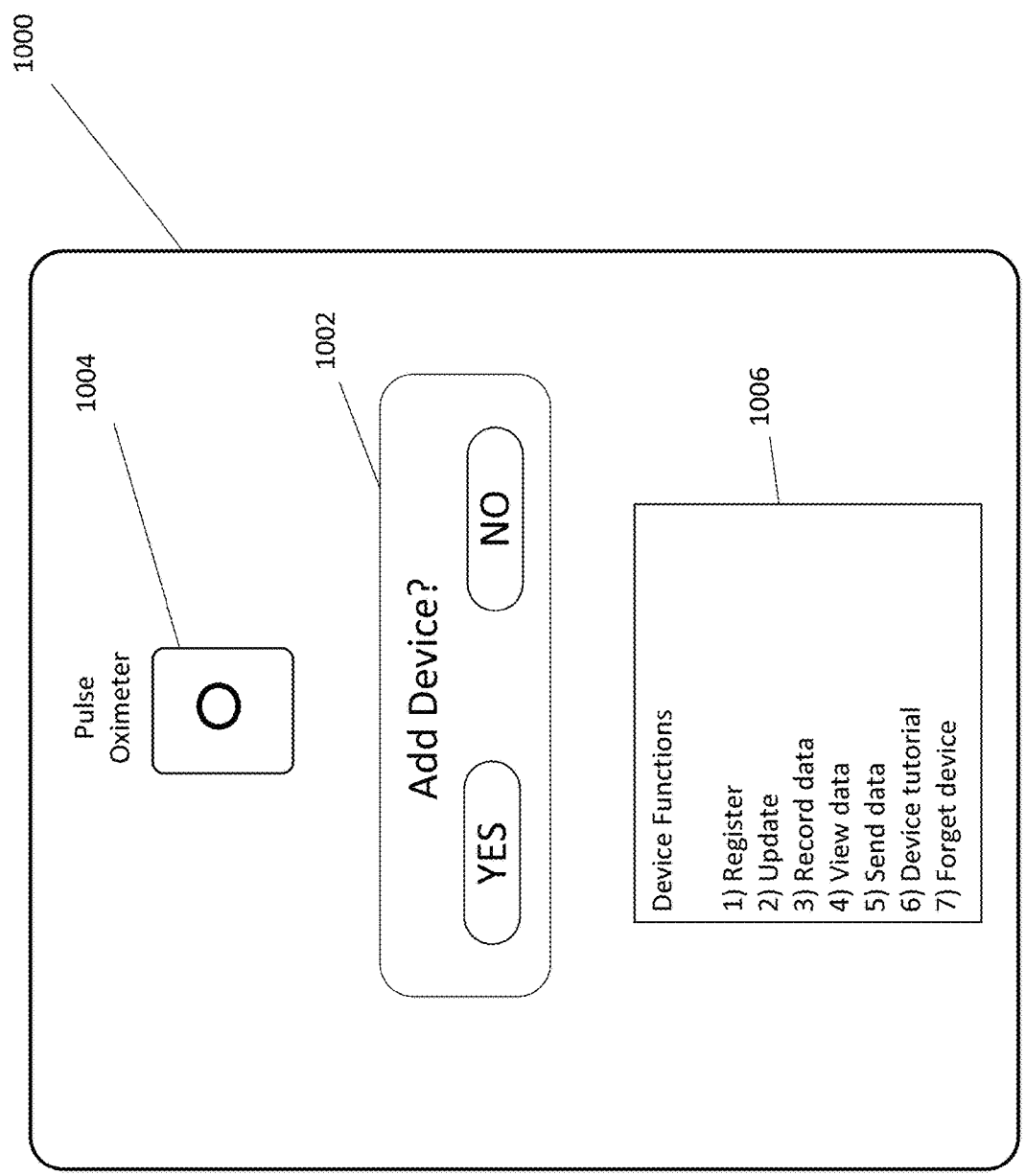
FIG. 10 shows an illustrative device management interface within the Sealthie configuration interface.

With reference now to FIG. 10, there is shown the exemplary device management interface 1000 within the configuration interface 712. The device management interface 1000 displays a specific device based upon a patient selection from the device inventory 900, or automatically as a result of the RHG 118 discovering or recognizing a device (e.g., pulse oximeter 1004) in the home domain 102 that does not exist in the device inventory 900. When such a new and unregistered device enters the home domain, a dialog box 1002 is presented requesting patient input to determine whether to add the new device to their device inventory 900. The device management interface 1000 also presents a device configuration menu 1006 to enable patients to configure newly added devices 1004. This device configuration menu 1006 may include register device (i.e., by scanning a device-specific QR code), update device software, record measurements and log information with the device 1004, view data measured by the device 1004, send data collected by the device to an external entity (i.e., healthcare organization systems 124, telehealth platform providers 126, healthcare providers 108), device tutorial, and forget the device (i.e., delete).

With reference now to FIG. 11, there is shown an illustrative augmented reality (AR) device tutorial 1100 presented through the configuration interface 712 and device inventory 900. In this embodiment, the device tutorial presented in the device configuration menu 1006 is a selectable AR tutorial for the particular device 1004. This AR tutorial may include an animation of the device 1102 superimposed on live video of the patient 1104 to present step by step instruction on use of the device 1004.

It is to be understood that the detailed description of illustrative embodiments are provided for illustrative purposes. Thus, the degree of software modularity for the transactional system and method presented above may evolve to benefit from the improved performance and lower cost of the future hardware components that meet the system and method requirements presented. The scope of the claims is not limited to these specific embodiments or examples. Therefore, various process limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A system for generating an individual digital healthcare representation, the system comprising:
   a remote healthcare gateway (RHG) client that is communicatively coupled to a home network access device;
   an RHG management server communicatively coupled to the RHG client via the home network access device;
   wherein the RHG client stores data generated by one or more home domain components and one or more cloud domain applications;
   the home domain components communicatively coupled to the RHG client over a local area network (LAN), wherein the home domain components includes at least one of a thermometer, a sphygmomanometer, an electrocardiogram machine, a pulse oximeter, a weight scale, an ultrasound machine, a glucose monitor, a skin analysis machine, a stethoscope, an autoscope, an orthopedic corrective therapy device, and a wellness monitoring wearable;
   the cloud domain applications communicatively coupled to the RHG client via the home network access device, wherein the cloud domain applications includes at least one of a healthcare organization systems, a telehealth platform provider, a medical device vendor servers, and a third-party security provider;
   wherein the RHG client operates as a central communications hub for the home domain components and the cloud domain applications;
   wherein the RHG client generates a continuously updated individual digital healthcare representation from the data associated with the home domain components and the cloud domain components; and
   a database associated with the RHG management server that is communicatively coupled to the RHG client, in which the RHG management server receives a plurality of healthcare data items including at least one of provider health records, an electronic health record, a genomic data, an exomic data, a medical device readings, a medical device report, a list of patient allergies, an inventory of patient medications, a pharmacy number, a prescriber, a strength, a dosage, a purpose, a side effect, a drug-drug interaction, an indication to alert clinicians to reactions, a quantity remaining, a timing for refills, and a questionnaire response.

2. The system of claim 1 wherein the RHG client includes an RHG smartphone application.

3. The system of claim 1 wherein the RHG client includes a data log of interactions with the home domain components and the cloud domain applications.

4. The system of claim 1 wherein the RHG client receives a plurality of historical data from the home domain components.

5. The system of claim 1 wherein the RHG management server generates at least one of a task alert, a security alert, a message alert, and a device alert.

6. The system of claim 1 wherein the RHG management server generates at least one of an instruction to perform an exercise, an instruction to take a medication, and an instruction to attend an appointment.

7. A remote healthcare gateway (RHG) client that generates an individual digital healthcare representation, RHG client comprising:
   a communication interface that is communicatively coupled to a home network access device;
   the RHG client stores data generated by one or more home domain components and one or more cloud domain applications;

the home domain components communicatively coupled to the RHG client over a local area network (LAN), wherein the home domain components includes at least one of a thermometer, a sphygmomanometer, an electrocardiogram machine, a pulse oximeter, a weight scale, an ultrasound machine, a glucose monitor, a skin analysis machine, a stethoscope, an autoscope, an orthopedic corrective therapy device, and a wellness monitoring wearable;

the cloud domain applications communicatively coupled to the RHG client via the home network access device, wherein the cloud domain applications includes at least one of a healthcare organization systems, a telehealth platform provider, a medical device vendor servers, and a third-party security provider;

wherein the RHG client operates as a central communications hub for the home domain components and the cloud domain applications;

wherein the RHG client generates a continuously updated individual digital healthcare representation from the data associated with the home domain components and the cloud domain components;

wherein the RHG client communicates with an RHG management server via the home network access device;

a database associated with the RHG management server that is communicatively coupled to the RHG client, in which the RHG management server receives a plurality of healthcare data items including at least one of provider health records, an electronic health record, a genomic data, an exomic data, a medical device readings, a medical device report, a list of patient allergies, an inventory of patient medications, a pharmacy number, a prescriber, a strength, a dosage, a purpose, a side effect, a drug-drug interaction, an indication to alert clinicians to reactions, a quantity remaining, a timing for refills, and a questionnaire response.

8. The RHG client of claim 7 wherein the RHG client includes an RHG smartphone application.

9. The RHG client of claim 7 wherein the RHG client includes a data log of interactions with the home domain components and the cloud domain applications.

10. The RHG client of claim 7 wherein the RHG client receives a plurality of historical data from the home domain components.

11. The RHG client of claim 7 wherein the RHG management server generates at least one of a task alert, a security alert, a message alert, and a device alert.

12. The RHG client of claim 7 wherein the RHG management server generates at least one of an instruction to perform an exercise, an instruction to take a medication, and an instruction to attend an appointment.

13. A method for generating an individual digital healthcare representation, the method comprising:

providing a remote healthcare gateway (RHG) client that is communicatively coupled to a home network access device;

storing, at the RHG client, data generated by one or more home domain components and one or more cloud domain applications;

communicatively coupling the home domain components to the RHG client over a local area network (LAN), wherein the home domain components includes at least one of a thermometer, a sphygmomanometer, an electrocardiogram machine, a pulse oximeter, a weight scale, an ultrasound machine, a glucose monitor, a skin analysis machine, a stethoscope, an autoscope, an orthopedic corrective therapy device, and a wellness monitoring wearable;

communicatively coupling the cloud domain applications to the RHG client via the home network access device, wherein the cloud domain applications includes at least one of a healthcare organization systems, a telehealth platform provider, a medical device vendor servers, and a third-party security provider;

enabling the RHG client to operate as a central communications hub for the home domain components and the cloud domain applications;

continuously updating the individual digital healthcare representation, at the RHG client, with data associated with the home domain components and the cloud domain components;

enabling the RHG client to communicate with an RHG management server via the home network access device;

causing a database, disposed at the RHG management server, to receive a plurality of healthcare data items including at least one of provider health records, an electronic health record, a genomic data, an exomic data, a medical device readings, a medical device report, a list of patient allergies, an inventory of patient medications, a pharmacy number, a prescriber, a strength, a dosage, a purpose, a side effect, a drug-drug interaction, an indication to alert clinicians to reactions, a quantity remaining, a timing for refills, and a questionnaire response.

14. The method of claim 13 wherein the RHG client includes an RHG smartphone application.

15. The method of claim 13 wherein the RHG client includes a data log of interactions with the home domain components and the cloud domain applications.

16. The method of claim 13 wherein the RHG client receives a plurality of historical data from the home domain components.

17. The method of claim 13 wherein the RHG management server generates at least one of a task alert, a security alert, a message alert, and a device alert.

18. The method of claim 13 wherein the RHG management server generates at least one of an instruction to perform an exercise, an instruction to take a medication, and an instruction to attend an appointment.

\* \* \* \* \*